US006426427B1

(12) United States Patent
Tonomura et al.

(10) Patent No.: US 6,426,427 B1
(45) Date of Patent: Jul. 30, 2002

(54) PREPARATION OF BISSILYLNORBORNANE COMPOUNDS

(75) Inventors: Yoichi Tonomura; Tohru Kubota; Mikio Endo, all of Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/935,659

(22) Filed: Aug. 24, 2001

(30) Foreign Application Priority Data

Aug. 25, 2000 (JP) ........................ 2000-255899

(51) Int. Cl.⁷ ................................ C07F 7/08
(52) U.S. Cl. ........................................ 556/431
(58) Field of Search ........................... 556/431

(56) References Cited

U.S. PATENT DOCUMENTS

| 5,151,538 A | * | 9/1992 | Hayashi et al. ............. 556/431 |
| 5,527,936 A | | 6/1996 | Dindi et al. |
| 5,719,251 A | * | 2/1998 | Wilczek et al. ......... 556/431 X |
| 6,268,456 B1 | * | 7/2001 | Gregorovich et al. ... 556/431 X |

FOREIGN PATENT DOCUMENTS

JP 11-500129 1/1999

OTHER PUBLICATIONS

The Preparation of Organosilicon Derivatives of Bicyclo–(2, 2,1)–Heptane, The Institute of Organic Chemistry of Academy of Sciences of the USSR, Vol. 31, No. 4, pp. 1199–1208, Apr. 1961.
Asymmetric Functionalization of Bicycloalkenes by Catalytic Enantioposition–Selective Hydrosilylation, Tetrahedron Letters, Vol. 33, No 47, pp. 7185–7188, 1992.

* cited by examiner

Primary Examiner—Paul F. Shaver
(74) Attorney, Agent, or Firm—Millen, White, Zelano & Branigan, P.C.

(57) ABSTRACT

A bissilylnorbornane compound is prepared by reacting 2,5-norbornadiene with a hydrogenchlorosilane in the presence of a mixture of a palladium compound and a phosphite or a palladium complex having a phosphate ligand as a catalyst. The bissilylnorbornane compound can be produced in high yields while suppressing formation of by-product nortricyclene.

20 Claims, No Drawings

PREPARATION OF BISSILYLNORBORNANE COMPOUNDS

BACKGROUND OF THE INVENTION

1. Technical Field

This invention relates to the preparation of bissilylnorbornane compounds by hydrosilylating 2,5-norbornadiene.

2. Background Art

Bissilylnorbornane compounds of the following general formula (2):

(2)

wherein "a" is 0, 1 or 2 have excellent properties including hardness and scratch resistance because of the norbornane skeleton within its molecule. They are thus useful as coupling agents to be added to paints for automotive painting and building painting, crosslinking agents and adhesives. They are also useful intermediates to alkoxysilane coupling agents.

For the preparation of these compounds, it is regarded best to start with 2,5-norbornadiene and add a hydrogenchlorosilane compound to the two double bonds in 2,5-norbornadiene. One such process using a radical initiator is disclosed in Japanese Publication of International Patent Application (JP-A) No. 11-500129. This process, however, has the drawbacks that there is a hazard because of the radical initiator having a risk of explosion, and reaction control is difficult. The radical initiator must be replenished in sequence, requiring complex steps. Moreover, the proportion of a bissilylated product, bistrichlorosilylnorbornane in the reaction solution is as low as 40%, and reactivity is poor. Thus the process is disadvantageous in industrial practice.

Other processes proposed thus far include reaction of 2,5-norbornadiene with a hydrogenchlorosilane compound in the presence of a platinum catalyst (J. Gen. Chem. USSR, 31, 4, 1109) and in the presence of a palladium catalyst (Tetrahedron Lett., 33 (1992), 7185). The former process relates to monosilylation, with the yield of monosilylated compound being as low as 44.3%. The low yield of the monosilylated compound of the following formula (4) is accounted to the formation of nortricyclene of the following formula (5).

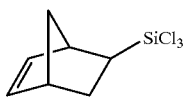
(4)

(5)

If the nortricyclene compound forms upon hydrosilylation of the monosilylated compound following monosilylation, the yield of the bissilylated compound becomes low because the nortricyclene compound is no longer hydrosilylated. To obtain the bissilylated compound in good yields, the formation of the nortricyclene compound must be minimized.

The latter process must use an organic phosphorus compound, which requires many stages of synthesis and is thus expensive, as a ligand to palladium atom. The reaction must be carried out at a low temperature over 24 hours in order to suppress the formation of the nortricyclene compound. If the temperature is raised to reduce the reaction time, more nortricyclene forms. The process is not advantageous to produce the desired compound on an industrial scale.

SUMMARY OF THE INVENTION

An object of the invention is to provide a process for preparing a bissilylnorbornane compound of formula (2) in an efficient and economical manner.

The invention is directed to a process for preparing a bissilylnorbornane compound of the following formula (2):

(2)

wherein "a" is 0, 1 or 2, by reacting 2,5-norbornadiene with a hydrogenchlorosilane compound of the following general formula (1):

$$HSi(CH_3)_aCl_{3-a} \quad (1)$$

wherein "a" is 0, 1 or 2. It has been found that when both a palladium compound and a phosphite are used as the catalyst, the formation of nortricyclene is minimized and the bissilylnorbornane compound of formula (2) is obtained C in high yields.

Therefore, the invention provides a process for preparing a bissilylnorbornane compound of the formula (2) by reacting 2,5-norbornadiene with a hydrogenchlorosilane compound of the formula (1) in the presence of a catalyst which is a mixture of a palladium compound and a phosphate or a palladium complex having a phosphate coordinated thereto.

DESCRIPTION OF THE PREFERRED EMBODIMENT

In the inventive process, the hydrogenchlorosilane compound used as a starting reactant has the general formula (1):

$$HSi(CH_3)_aCl_{3-a} \quad (1)$$

wherein "a" is 0, 1 or 2. Illustrative of the compound are trichlorosilane, methyldichlorosilane and dimethylchlorosilane.

The blending ratio of the hydrogenchlorosilane compound to 2,5-norbornadiene is not critical although it is preferred from the reactivity and productivity standpoints to use 1.0 to 3.0 mol, especially 1.5 to 2.5 mol of the hydrogenchlorosilane compound per mol of 2,5-norbornadiene.

Examples of the palladium compound used herein include palladium acetate, palladium chloride, sodium palladium chloride, dichlorobis(benzonitrile)palladium, dichloro(1,5-cyclooctadiene)palladium, and di-R-chlorobis(π-allyl) dipalladium.

The amount of the palladium compound used is not critical although it is preferred from the reactivity and productivity standpoints to use 0.000001 to 0.01 mol, especially 0.00001 to 0.001 mol of the palladium compound per mol of 2,5-norbornadiene. Less than 0.000001 mol of the palladium compound may fail to develop the desired catalysis whereas more than 0.01 mol of the palladium compound may fail to achieve a reaction promoting effect enough to compensate for such increments.

Illustrative examples of the phosphite include trimethyl phosphite, triethyl phosphite, tripropyl phosphite, tributyl phosphite, truisobutyl phosphite, tripentyl phosphite, trineopentyl phosphite, tri(2-ethylhexyl)phosphite, truisopropyl phosphite, tri-s-butyl phosphite, tri-t-butyl phosphite, tri-t-amyl phosphite, tricyclopentyl phosphite, tricyclohexyl phosphite, triphenyl phosphite, tribenzyl phosphite, tris(trimethylsilylmethyl)phosphite, tris(1-trimethylsilylethyl)phosphite, tris(2-trimethylsilylethyl)phosphite, and tris(3-trimethylsilylpropyl)phosphite. From the reactivity and selectivity standpoints, compounds of the following general formula (3) are especially preferred.

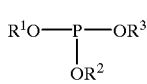

(3)

Herein $R^1$, $R^2$ and $R^3$, which may be the same or different, are substituted or unsubstituted monovalent hydrocarbon groups having 1 to 10 carbon atoms. At least one of $R^1$, $R^2$ and $R^3$ is a branched aliphatic monovalent hydrocarbon group, cyclic aliphatic monovalent hydrocarbon group or trialkylsilyl-substituted aliphatic monovalent hydrocarbon group.

The substituted or unsubstituted monovalent hydrocarbon groups include straight, branched or cyclic aliphatic monovalent hydrocarbon groups, preferably straight, branched or cyclic alkyl groups, aryl groups and aralkyl groups, and trialkylsilyl-substituted monovalent hydrocarbon groups corresponding to the foregoing hydrocarbon groups in which one or more hydrogen atoms thereon are substituted with trialkylsilyl groups, especially trialkylsilyl-substituted aliphatic monovalent hydrocarbon groups. Illustrative examples include methyl, ethyl, propyl, n-butyl, pentyl, hexyl, phenyl, benzyl, isopropyl, isobutyl, s-butyl, t-butyl, neopentyl, isoamyl, t-amyl, 2-ethylhexyl, cyclobutyl, cyclopentyl, cyclohexyl, trimethylsilylmethyl, 1-trimethylsilylethyl, 2-trimethylsilylethyl and 3-trimethylsilylpropyl.

At least one of $R^1$, $R^2$ and $R^3$ is a branched aliphatic hydrocarbon group, cyclic aliphatic hydrocarbon group or trialkylsilyl-substituted aliphatic hydrocarbon group, for example, isopropyl, isobutyl, s-butyl, t-butyl, neopentyl, isoamyl, t-amyl, 2-ethylhexyl, cyclobutyl, cyclopentyl, cyclohexyl, trimethylsilylmethyl, 1-trimethylsilylethyl, 2-trimethylsilylethyl or 3-trimethylsilylpropyl.

Illustrative preferred examples of the phosphite of the formula (3) include triisopropyl phosphite, tri-s-butyl phosphite, tricyclohexyl phosphite, tris(trimethylsilylmethyl)phosphite, tris(1-trimethylsilylethyl)phosphite, tris(2-trimethylsilylethyl)phosphite, and tris(3-trimethylsilylpropyl)phosphite. Of these, triisopropyl phosphite and tri-s-butyl phosphite are especially preferred.

The amount of the phosphite used is not critical although it is preferred to use 1 to 4 mol of the phosphite per mol of palladium atom in the palladium compound. Less than 1 mol of the phosphite may lead to a lowering of reaction selectivity whereas more than 4 mol of the phosphite may lead to a loss of catalytic activity.

Instead of using the palladium compound in admixture with the phosphate, a complex may be used which is obtained by premixing the palladium compound with the phosphate and effecting reaction between them. If desired, the resulting complex is isolated and purified prior to use.

Illustrative examples of the complex include palladium dichlorobistriethyl phosphite, palladium dichlorobistriisopropyl phosphite, palladium dichlorobistri-s-butyl phosphate, and palladium dichlorobistricyclohexyl phosphate. The amount of the complex used may be similar to that of the palladium compound.

For reaction of 2,5-norbornadiene with hydrogenchlorosilane to take place, the reaction temperature is preferably 0C to 200° C., especially 10° C. to 140° C., under atmospheric pressure or applied pressure, though not critical.

Although the reaction proceeds in a solventless system, a solvent may be used. Exemplary suitable solvents used herein include hydrocarbon solvents such as pentane, hexane, cyclohexane, benzene, toluene, and xylene, ether solvents such as diethyl ether, tetrahydrofuran, and dioxane, ester solvents such as ethyl acetate and butyl acetate, aprotic polar solvents such as acetonitrile, and chlorinated hydrocarbon solvents such as dichloromethane and chloroform. These solvents may be used alone or in admixture of any.

The aforementioned reaction yields an organosilicon compound of the general formula (2):

(2)

wherein "a" is 0, 1 or 2. Illustrative of the compound are bis(trichlorosilyl)norbornane, bis(methyldichlorosilyl)norbornane, and bis(dimethylchlorosilyl)norbornane.

EXAMPLE

Examples of the invention are given below by way of illustration and not by way of limitation.

Example 1

A flask equipped with a stirrer, reflux condenser, dropping funnel and thermometer was charged with 92.1 g (1.0 mol) of 2,5-norbornadiene, 28.61 mg of dichloro(cyclooctadiene)palladium and 50.1 mg of tri-s-butyl phosphite and heated at 80° C. After the internal temperature became stabilized, 271.0 g (2.0 mol) of trichlorosilane was added dropwise over 5 hours. After the completion of dropwise addition, the reaction solution was stirred at 80° C. for one hour. The reaction solution was distilled, collecting 283.1 g of bis(trichlorosilyl)norbornane as a fraction having a boiling point of 110–115° C./27 Pa (yield 78%).

Example 2

A flask equipped with a stirrer, reflux condenser, dropping funnel and thermometer was charged with 92.1 g (1.0 mol) of 2,5-norbornadiene, 28.6mg of dichloro(cyclooctadiene) palladium and 41.6 mg of triisopropyl phosphite and heated at 80° C. After the internal temperature became stabilized, 271.0 g (2.0 mol) of trichlorosilane was added dropwise over 5 hours. After the completion of dropwise addition, the reaction solution was stirred at 80° C. for one hour. The reaction solution was distilled, collecting 268.7 g of bis(trichlorosilyl)norbornane as a fraction having a boiling point of 110–115° C./27 Pa (yield 74%).

Example 3

A flask equipped with a stirrer, reflux condenser, dropping funnel and thermometer was charged with 92.1 g (1.0 mol)

of 2,5-norbornadiene, 28.6mg of dichloro(cyclooctadiene) palladium and 33.2 mg of triethyl phosphite and heated at 80° C. After the internal temperature became stabilized, 271.0 g (2.0 mol) of trichlorosilane was added dropwise over 5 hours. After the completion of dropwise addition, the reaction solution was stirred at 80° C. for one hour. The reaction solution was distilled, collecting 235.7 g of bis (trichlorosilyl)norbornane as a fraction having a boiling point of 110–115° C./27 Pa (yield 65%).

Comparative Example 1

A flask equipped with a stirrer, reflux condenser, dropping funnel and thermometer was charged with 92.1 g (1.0 mol) of 2,5-norbornadiene, 28.6mg of dichloro(cyclooctadiene) palladium and 52.5 mg of triphenyl phosphine and heated at 80° C. After the internal temperature became stabilized, 271.0 g (2.0 mol) of trichlorosilane was added dropwise over 5 hours. At the end of dropwise addition, refluxing of unreacted trichlorosilane was observed. After the completion of dropwise addition, the reaction solution was stirred at 80° C. for one hour. The reaction solution was distilled, collecting 159.7 g of bis(trichlorosilyl)norbornane as a fraction having a boiling point of 110–115° C./27 Pa (yield 44%).

Comparative Example 2

A flask equipped with a stirrer, reflux condenser, dropping funnel and thermometer was charged with 92.1 g (1.0 mol) of 2,5-norbornadiene, 28.6mg of dichloro(cyclooctadiene) palladium and 93.7 mg of 2-(diphenylphosphino)-2'-methoxy-1,1'-binaphthyl and heated at 800° C. After the internal temperature became stabilized, 271.0 g (2.0 mol) of trichlorosilane was added dropwise over 5 hours. At the end of dropwise addition, refluxing of unreacted trichlorosilane was observed. After the completion of dropwise addition, the reaction solution was stirred at 80° C. for one hour. The reaction solution was distilled, collecting 165.3 g of bis (trichlorosilyl)norbornane as a fraction having a boiling point of 110–115° C./27 Pa (yield 4%).

Reference Example 1

Synthesis of bis(trimethoxysilyl)norbornane

A flask equipped with a stirrer, reflux condenser, dropping funnel and thermometer was charged with 181.6 g (0.5 mol) of bis(trichlorosilyl)norbornane synthesized in Example 1, 364.4 g (3.6mol) of triethylamine and 1,000 ml of toluene and heated at 50° C. After the internal temperature became stabilized, 115.2 g (3.6 mol) of methanol was added dropwise over 5 hours. After the completion of dropwise addition, the reaction solution was stirred at 70° C. for 2 hours. The reaction solution was cooled to room temperature whereupon the resulting salt was removed by filtration and the filtrate was distilled. There was collected 154.3 g of bis(trimethoxysilyl)norbornane as a fraction having a boiling point of 113–117° C./27 Pa (yield 92%).

There has been described a process of producing bissilylnorbornane compounds in high yields while suppressing formation of by-product nortricyclene which causes low yields.

Japanese Patent Application No. 2000-255899 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A process for preparing a bissilylnorbornane compound of the following general formula (2):

(2)

wherein "a" is 0, 1 or 2, by reacting 2,5-norbornadiene with a hydrogenchlorosilane compound of the following general formula (1):

$$HSi(CH_3)_aCl_{3-a}$$ (1)

wherein "a" is 0, 1 or 2 in the presence of a catalyst which is a mixture of a palladium compound and a phosphite or a palladium complex having a phosphate coordinated thereto.

2. The process of claim 1 wherein the phosphite has the following general formula (3):

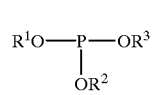

(3)

wherein $R^1$, $R^2$ and $R^3$, which may be the same or different, are substituted or unsubstituted monovalent hydrocarbon groups having 1 to 10 carbon atoms, at least one of $R^1$, $R^2$ and $R^3$ being a branched aliphatic monovalent hydrocarbon group, cyclic aliphatic monovalent hydrocarbon group or trialkylsilyl-substituted aliphatic monovalent hydrocarbon group.

3. The process of claim 1 wherein the hydrogenchlorosilane compound of formula (1) is trichlorosilane.

4. The process of claim 1 wherein the hydrogenchlorosilane compound of formula (1) is methyldichlorosilane or dimethylchlorosilane.

5. The process of claim 1 wherein 0.1 to 0.3 mol of the hydrogenchlorosilane is reacted with 1 mol of 2,5-norbornadiene.

6. The process of claim 1 wherein 1.5 to 2.5 mol of the hydrogenchlorosilane is reacted with 1 mol of 2,5-norbornadiene.

7. The process of claim 1 wherein the compound of formula (2) bis(trichlorosilyl)norbornane, bis(methyldichlorosily)norbornane or bis(dimethylchlorosilyl)norbornane.

8. The process of claim 1 carried out at a temperature of 0° C. to 200° C.

9. The process of claim 1 carried out at a temperature of 10° C. to 140° C.

10. The process of claim 1 carried out in the presence of a solvent.

11. The process of claim 2, wherein the compound of formula (3) is triisopropyl phosphite, tri-s-butyl phosphite, tricyclohexyl phosphite, tris(trimethyl-silylmethyl) phosphite, tris(1-trimethylsilyethyl) phosphite, tris(2-trimethylsilylethyl) phosphite or tris(3-trimethylsilylpropyl) phosphite.

12. The process of claim 2, wherein the compound of formula (3) is triisopropyl phosphite or tri-s-butyl phosphite.

13. The process of claim 1, wherein the palladium compound is palladium acetate, palladium chloride, sodium palladium chloride, dichlorobis(benzonitrile)palladium, dichloro(1,5-cyclooctadiene)palladium or di-$\mu$-chlorobis($\pi$-allyl)dipalladium.

14. The process of claim 1, wherein the phosphite is trimethyl phosphite, triethyl phosphite, tripropyl phosphite, tributyl phosphite, triisobutyl phosphite, tripentyl phosphite, trineopentyl phosphite, tri(2-ethylhexyl) phosphite, triisopropyl phyosphite, tri-s-butyl phosphite, tri-t-butyl phosphite, tri-t-amyl phosphite, tricyclopentyl phosphite. tricyclohexyl phosphite, triphenyl phosphite, tribenzyl phosphite, tris(trimethylsilylmethyl) phosphite, tris(1-trimethylsilylethyl) phosphite, tris(2-trimethylsilylethyl) phosphite or tris(3-trimethylsilylpropyl) phosphite.

15. The process of claim 1, wherein the palladium complex having a phosphite coordinated thereto is palladium dichlorobistriethyl phosphite, palladium dichlorobistriisopropyl phosphite, palladium dichlorobistri-s-butyl phosphite or palladium dichlorobistricyclohexyl phosphite.

16. The process of claim 1 wherein 0.000001 to 0.01 mol of the palladium compound or palladium complex is present per mol of 2,5-norbornadiene.

17. The process of claim 1 wherein 0.00001 to 0.01 mol of the palladium compound or palladium complex is present per mol of 2,5-norbornadiene.

18. The process of claim 1 wherein 1 to 4 mol of phosphite is present per mol of palladium atom in the palladium compound.

19. The process according to claim 2, wherein $R^1$, $R^2$ and $R^3$, which may be the same or different, are methyl, ethyl, propyl, n-butyl, pentyl, hexyl, phenyl, benzyl, isopropyl, isobutyl, s-butyl, t-butyl, neopentyl, isoamyl, t-amyl, 2-ethylhexyl, cyclobutyl, cyclopentyl, cyclohexyl, trimethylsilylmethyl, 1-trimethylsilylethyl, 2-trimethylsilylethyl or 3-trimethylsilylproply, and wherein at least one of $R^1$, $R^2$ and $R^3$ is isopropyl, isobutyl, s-butyl, t-butyl, neopentyl, isoamyl, t-amyl, 2-ethylhexyl, cyclobutyl, cyclopentyl, cyclohexyl, trimethylsilylmethyl, 1-trimethylsilylethyl, 2-trimethylsilylethyl or 3-trimethylsilylpropyl.

20. The process of claim 1, wherein the compound of formula (2) bis(trichlorosilyl)norbornane.

* * * * *